United States Patent [19]

Ogawa et al.

[11] 4,261,970
[45] Apr. 14, 1981

[54] THEOPHYLLINE SUSTAINED RELEASE GRANULE

[75] Inventors: Keizaburo Ogawa; Tadashi Ukigaya, both of Kawagoe; Satoru Tanaka, Urawa, all of Japan

[73] Assignee: Nikken Chemicals Co., Ltd., Tokyo, Japan

[21] Appl. No.: 109,082

[22] Filed: Jan. 2, 1980

[30] Foreign Application Priority Data

May 18, 1979 [JP] Japan ................................. 54/61294

[51] Int. Cl.³ .......................... A61K 9/22; A61K 9/36; A61K 31/52
[52] U.S. Cl. ...................................... 424/19; 424/22; 424/35; 424/253
[58] Field of Search ................................. 424/19–22, 424/35, 38

[56] References Cited

U.S. PATENT DOCUMENTS

| | | | |
|---|---|---|---|
| 2,928,769 | 3/1960 | Gaunt | 424/22 |
| 3,062,720 | 11/1962 | Costello | 424/22 |
| 3,079,303 | 2/1963 | Raff et al. | 424/33 |
| 3,101,293 | 8/1963 | Gaunt et al. | 424/22 |
| 3,102,845 | 9/1963 | Fennell | 424/22 |
| 3,115,441 | 12/1963 | Hermelin | 424/22 |
| 3,133,863 | 5/1964 | Tansey | 424/19 |
| 3,136,695 | 6/1964 | Tansey | 424/22 |
| 3,148,124 | 9/1964 | Gaunt | 424/19 |
| 3,629,393 | 12/1971 | Nakamoto et al. | 424/22 |
| 3,773,920 | 11/1973 | Nakamoto et al. | 424/19 |

Primary Examiner—Shep K. Rose
Attorney, Agent, or Firm—Oblon, Fisher, Spivak, McClelland & Maier

[57] ABSTRACT

A Theophylline sustained release granule comprises 10 to 45 wt. % of Theophylline, 30 to 60 wt. % of a metal salt of higher fatty acid and 0.5 to 10 wt. % of ethyl cellulose at a ratio of 1:1 to 1:3 by weight of Theophylline to said metal salt of higher fatty acid.

The Theophylline sustained release granule is effective for maintaining a suitable concentration of Theophylline in blood for a long time.

4 Claims, No Drawings

THEOPHYLLINE SUSTAINED RELEASE GRANULE

BACKGROUND OF THE INVENTION

1. Field of the Invention

The present invention relates to a Theophylline sustained release granule which maintains suitable blood level of Theophylline.

2. Description of the Prior Arts

Theophylline has been used for therapy and prevention of asthma as a bronchodilator. Recently, pharmacological, biopharmaceutical and clinical studies of Theophylline have been developed to find the fact of the optimum concentration of Theophylline in blood which give satisfactory medical effect and low probability of side-effect. Therefore, the advantageous effect of Theophylline has been further recognized.

The side-effects of Theophylline may cause nausea or headache in high probability and also may cause unquietness, convulsion and tachycardia. These side-effects are caused depending upon a concentration of Theophylline in blood.

The medication of Theophylline is continued for a long period so as to prevent fits in chronic asthma. Therefore, it is important to give a precise plane for medication so as to maintain the optimum concentration of Theophylline in blood.

It is optimum to consider the medication of Theophylline at a dose suitable for individual patient each four to six hours. It is not so easy to continue such frequent medications everyday.

In such case, a sustained release medical composition is remarkably advantageous so as to minimize times of medication and to prevent sudden increase of a concentration of Theophylline in blood.

The other important problem in a therapy by the medication of Theophylline is that speeds of metabolism and discharge of Theophylline are highly different for each patient. It has been reported that a biological half-life of Theophylline in blood differs in a range of 3 to 9.5 hours. Therefore, it is preferable to determine each optimum dose by a quantative measurement of a concentration of Theophylline in blood for each patient. In view of the characteristics of medication of Theophylline, it is suitable to select a form of a composition which can sustain the effect of Theophylline and can easily select a dose of Theophylline to give a desired dose especially a sustained release granule in a medication for chronic asthma.

SUMMARY OF THE INVENTION

It is an object of the present invention to provide a Theophylline sustained release granule which is useful for maintaining an optimum concentration of Theophylline in blood.

The foregoing and other objects of the present invention have been attained by providing a Theophylline sustained release granule which comprises 10 to 45 wt.% of Theophylline, 30 to 60 wt.% of a metal salt of higher fatty acid and 0.5 to 10 wt.% of ethyl cellulose at a ratio of 1:1 to 1:3 by weight of Theophylline to said metal salt of higher fatty acid.

DETAILED DESCRIPTION OF THE PREFERRED EMBODIMENTS

The inventors have prepared various kinds of sustained release granules containing Theophylline so as to obtain a Theophylline sustained release granule which is optimum for said medication of Theophylline.

As a result, the inventors have found that a granule which can gradually release Theophylline at a stable rate for a long time can be obtained by combining Theophylline, a metal salt of higher fatty acid and ethyl cellulose at suitable ratios and kneading and granulating the mixture by a conventional simple method. The present invention has been attained by the finding.

In the present invention, if necessary, a suitable amount of another adjuvant can be incorporated into said granule comprising Theophylline, the metal salt of higher fatty acid and ethyl cellulose at said ratios. The adjuvant can be incorporated at a ratio of up to about 50 wt.% of the granule.

Suitable metal salts of higher fatty acid include metal salts such as magnesium, calcium and aluminum of stearic acid, palmitic acid, oleic acid and myristic acid.

An alkali metal salt such as sodium and potassium salts, is not suitable when no other metal compound is added.

The other adjuvant can be a conventional adjuvant such as starch, lactose, crystalline cellulose, hydroxypropyl starch and sugar.

The Theophylline sustained release granule of the present invention is prepared by mixing Theophylline and a metal salt of higher fatty acid if necessary, with the other adjuvant; adding an organic solvent solution of ethyl cellulose to the mixture; kneading it, and granulating the kneaded mixture by a conventional method such as an extrusion-granulating machine; and drying and screening of grain.

It is necessary to combine Theophylline, the metal salt of higher fatty acid and ethyl cellulose at said ratios in the granule.

The organic solvent used for dissolving ethyl cellulose can be ethanol, isopropyl alcohol, methylene chloride, dichloroethane, etc. It is optimum to use ethanol.

The release speed of Theophylline from the Theophylline sustained release granule is mainly depending upon the ratios of Theophylline, the metal salt of higher fatty acid and ethyl cellulose.

When the organic solvent solution of ethyl cellulose is added as a binder to the metal salt of higher fatty acid and the mixture is kneaded and granulated, a hydrophobic granule which has high bulk density is prepared. Therefore, the release speed of Theophylline is decreased depending upon an increase of the contents of the metal salt of higher fatty acid and ethyl cellulose in the granule, whereas the release speed of Theophylline is increased depending upon a decrease of the contents of the metal salt of higher fatty acid and ethyl cellulose. Therefore, in order to maintain a stable release speed of Theophylline for a long time, it is preferable to combine Theophylline, the metal salt of higher fatty acid and ethyl cellulose at said ratios in the granule. A Theophylline sustained release granule having suitable release speed can not be obtained out of said range of the contents of Theophylline, the metal salt of higher fatty acid and ethyl cellulose.

A particle size of the granule is preferably in a range of 0.6 to 1.2 mm of a diameter and 1 to 3 mm of a length as the granule prepared by an extrusion-granulating machine in view of the stable release speed of Theophylline for a long time and the easy preparation of the granule.

The Theophylline sustained release granule of the present invention can be further coated by a conventional film coating with hydroxypropyl methyl cellulose or by a conventional sugar coating, if necessary.

The Theophylline sustained release of the present invention has the advantages that the uniformity the release speed of Theophylline is high without an affect of pH of a digestive juice or an emzyme and the dissolution of Theophylline is substantially completed.

In the practical oral medication, a concentration of Theophylline in blood can be maintained at high level in stable for a long time such as longer than 12 hours. Therefore, the times of the medication can be advantageously decreased to twice or less per day.

The Theophylline sustained release granule of the present invention can be easily prepared by a conventional granulating machine such as an extrusion-granulating machine. The cost for the preparation of the granule is low. All of the materials used for the preparation of the granule can be the materials which are already approved by Japanese Phamacopoeia-IX and Japanese Standards of Food Additives-IV to have high safety and to be low cost.

The present invention will be further illustrated by certain examples showing the process for preparing the Theophylline sustained release granules and the release speeds of Theophylline from the granules and results of measurements of concentrations of Theophylline in blood after each oral medication.

EXAMPLE 1

1605 Ml. of a solution of 5% (W/V) of ethyl cellulose (Ethocel-Standard-100 ®) manufactured by Dow Chemical) in ethanol was added to a mixture of 1500 g of Theophylline, 625 g of lactose and 1875 g of calcium stearate and the mixture was kneaded and granulated by an extrusion-granulating machine equipped with a basket having a size of 1.0 mm. The granule was dried at 55° C. and dressed by a 16 mesh sieve (all grains were passed through the 16 mesh sieve) by rubbing fine and the resulting granules were seived by a 32 mesh sieve to remove fine powder (32 mesh pass) and to obtain 3825 g of a Theophylline sustained release granule.

EXAMPLE 2

1270 Ml. of a solution of 5% (W/V) of ethyl cellulose (Ethocel-Standard-100 ®) in ethanol was added to a mixture of 2160 g of Theophylline, 1440 g of lactose and 2160 g of calcium stearate. The mixture was kneaded and granulated as set forth in Example 1 to obtain 4420 g of a Theophylline sustained release granule.

EXAMPLE 3

225 Ml. of a solution of 5% (W/V) of ethyl cellulose (Ethocel-Standard-100 ®) in ethanol was added to a mixture of 150 g of Theophylline, 165 g of lactose and 412.5 g of calcium stearate. The mixture was kneaded and granulated as set forth in Example 1 to obtain a Theophylline sustained release granule.

EXAMPLE 4

114 Grams of a solution of 25% (W/W) of ethyl cellulose (Ethocel-Standard-10 ®) in ethanol was added to a mixture of 108 g of Theophylline, 72 g of lactose and 108 g of calcium stearate. The mixture was kneaded and granulated as set forth in Example 1 to obtain a Theophylline sustained release granule.

EXAMPLE 5

Release tests for the granules prepared in Examples 1 to 4 at 37° C. were carried out. The results are shown in Table 1. In the release test, the percent of release of Theophylline in the standard solution (pH=1.2) which was obtained by dissolving 2.0 g of sodium chloride with 24.0 ml. of 10% (W/V) diluted hydrochloric acid and water to be 1000 ml., was measured for the initial one time and then, the percent of release of Theophylline in the standard solution (pH=7.5) which was obtained by dissolving 35.8 g of $Na_2HPO_4.12H_2O$, with 6.0 ml. of 10% (W/V) diluted hydrochloric acid and water to be 1000 ml., was measured from one hour to eight hours.

TABLE 1

| Time (hour) | 1 | 2 | 4 | 6 | 8 |
|---|---|---|---|---|---|
| Granule of Example 1 | 20.0 | 46.0 | 68.0 | 80.0 | 91.5 |
| Granule of Example 2 | 34.0 | 63.0 | 87.0 | 97.0 | 100 |
| Granule of Example 3 | 26.0 | 40.0 | 56.5 | 68.5 | 77.5 |
| Granule of Example 4 | 30.9 | 48.5 | 71.3 | 84.6 | 91.5 |

EXAMPLE 6

Each mixture of Theophylline sustained release granule prepared in Example 1 and the Theophylline sustained release granule prepared in Example 2 (1:1 by weight) was orally administrated for 5 adult males at each dose of 6 mg/kg as Theophylline and each concentration of Theophylline in blood was periodically measured. The average concentrations of Theophylline in blood are shown in Table 2.

TABLE 2

| Time (hour) | 2 | 4 | 6 | 8 | 10 | 12 |
|---|---|---|---|---|---|---|
| Concentration of Theophylline in blood ($\mu$g/ml. = serum) | 6.1 | 7.3 | 8.5 | 8.3 | 7.8 | 7.4 |

We claim:

1. A Theophylline containing sustained release granule having a diameter of from about 0.6 to about 1.2 mm and a length of from about 1 to about 3 mm which comprises from 10 to 45 wt.% Theophylline, from 30 to 60 wt.% of a metal salt of a higher fatty acid selected from the group consisting of magnesium, calcium and aluminium salts of stearic acid, palmitic acid, oleic acid and myristic acid and from 0.5 to 10 wt.% of ethyl cellulose, the ratio by weight of Theophylline to said metal salt of a higher fatty acid being from 1:1 to 1:3.

2. The Theophylline sustained release granule according to claim 1, wherein the granule additionally contains a pharmaceutically acceptable adjunct in an amount not exceeding 50 wt.%.

3. The Theophylline sustained release granule according to claim 2, wherein said pharmaceutically acceptable adjuvant is selected from the group consisting of starch, lactose, crystalline cellulose, hydroxypropyl starch and sugar.

4. The Theophylline sustained release granule according to claim 1, wherein said granule is coated with a pharmaceutically acceptable coating material selected from the group consisting of hydroxypropyl methyl cellulose and sugar.

* * * * *